US009271777B2

(12) United States Patent
Nichols et al.

(10) Patent No.: US 9,271,777 B2
(45) Date of Patent: Mar. 1, 2016

(54) UNILATERAL MOVEABLE INTERBODY FUSION DEVICE AND METHOD OF USE

(71) Applicant: Biomet Spine, LLC, Broomfield, CO (US)

(72) Inventors: Ross R. Nichols, North Webster, IN (US); Brian G. Emerick, Columbia City, IN (US); Daniel Refai, Atlanta, GA (US)

(73) Assignee: Biomet Spine, LLC, Broomfield, CO (US)

( * ) Notice: Subject to any disclaimer, the term of this patent is extended or adjusted under 35 U.S.C. 154(b) by 406 days.

(21) Appl. No.: 13/715,448

(22) Filed: Dec. 14, 2012

(65) Prior Publication Data

US 2013/0158668 A1   Jun. 20, 2013

Related U.S. Application Data

(60) Provisional application No. 61/570,613, filed on Dec. 14, 2011.

(51) Int. Cl.
| A61B 17/88 | (2006.01) |
| A61F 2/44 | (2006.01) |
| A61F 2/46 | (2006.01) |
| A61B 17/56 | (2006.01) |
| A61F 2/30 | (2006.01) |
| A61F 2/28 | (2006.01) |

(52) U.S. Cl.
CPC ............... *A61B 17/88* (2013.01); *A61B 17/56* (2013.01); *A61F 2/44* (2013.01); *A61F 2/447* (2013.01); *A61F 2/4455* (2013.01); *A61F 2/46* (2013.01); *A61F 2/4603* (2013.01); *A61F 2/4611* (2013.01); *A61B 2017/564* (2013.01); *A61F 2002/2835* (2013.01); *A61F 2002/304* (2013.01); *A61F 2002/3037* (2013.01); *A61F 2002/3052* (2013.01); *A61F 2002/30112* (2013.01); *A61F 2002/30329* (2013.01); *A61F 2002/30398* (2013.01); *A61F 2002/30401* (2013.01); *A61F 2002/30418* (2013.01); *A61F 2002/30518* (2013.01); *A61F 2002/30523* (2013.01); *A61F 2002/30556* (2013.01); *A61F 2002/30579* (2013.01); *A61F 2002/30601* (2013.01); *A61F 2002/30604* (2013.01); *A61F 2002/30607* (2013.01); *A61F 2002/30616* (2013.01); *A61F 2002/30772* (2013.01); *A61F 2002/30904* (2013.01); *A61F 2002/4625* (2013.01); *A61F 2002/4627* (2013.01)

(58) Field of Classification Search
CPC .. A61B 17/56; A61B 2017/564; A61B 17/88; A61F 2002/30329; A61F 2002/30518; A61F 2002/30523; A61F 2002/30589; A61F 2002/30601; A61F 2002/30604; A61F 2002/30904; A61F 2/44; A61F 2/4455; A61F 2/447; A61F 2/46; A61F 2/4603; A61F 2/4611; A61F 2002/4625; A61F 2002/4627

See application file for complete search history.

(56) References Cited

U.S. PATENT DOCUMENTS 5,658,335 A * 8/1997 Allen ..................... 623/17.16
6,176,882 B1 * 1/2001 Biedermann et al. ...... 623/17.15

(Continued)

*Primary Examiner* — Larry E Waggle, Jr.
(74) *Attorney, Agent, or Firm* — Schwegman Lundberg & Woessner, P.A.

(57) ABSTRACT

An interbody fusion device including a body member, at least one side member engaging the body member, and at least one movement mechanism that engages at least one side member and the body member. A surgical method for maintaining a space between two vertebral bodies in a spine, including the steps of obtaining a medical device, such as an interbody fusion device, and inserting and coupling an expansion tool into an opening within the medical device. The surgical method also including slidingly inserting the medical device into a space between two vertebral bodies and rotating the expansion tool to move the at least one side member in a direction relative to the body member. The method may further include detaching the expansion tool from the medical device and removing the tool from the space between the two vertebral bodies in the spine.

18 Claims, 16 Drawing Sheets

(56) References Cited

U.S. PATENT DOCUMENTS

| | | | |
|---|---|---|---|
| 6,723,126 B1 * | 4/2004 | Berry | 623/17.11 |
| 6,953,477 B2 | 10/2005 | Berry | |
| 2006/0224241 A1 * | 10/2006 | Butler et al. | 623/17.15 |
| 2007/0198089 A1 * | 8/2007 | Moskowitz et al. | 623/17.11 |
| 2012/0310350 A1 * | 12/2012 | Farris et al. | 623/17.16 |

* cited by examiner

UNILATERAL MOVEABLE INTERBODY FUSION DEVICE AND METHOD OF USE

CROSS REFERENCE TO RELATED APPLICATION

This application claims priority benefit under 35 U.S.C. §119(e) of U.S. provisional patent application No. 61/570,613 filed Dec. 14, 2011, which is incorporated herein by reference in its entirety.

TECHNICAL FIELD

The present invention relates generally to general surgery, orthopaedic and neurosurgical implants used for insertion within a space between hard tissue structures, and more specifically, but not exclusively, concerns devices implanted between bones to replace a resected, fractured or diseased structures and to maintain or reestablish proper spacing between two bones.

BACKGROUND OF THE INVENTION

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY OF THE INVENTION

Advancement of the state of interbody fusion devices and implants and the surgical management relating to the clinical presentation of damaged tissue structures within the body is believed desirable. Example embodiments of the invention that satisfies the need for improvements to an expandable interbody fusion device used to treat patients suffering from either diseased or damaged disc or other tissue structures includes at least one moveable side member coupled to a body member.

The present invention provides in one aspect, an interbody fusion device having a body member, at least one side member engaging the body member and at least one movement mechanism engaging the at least one side member and the body member.

The present invention provides in another aspect, a surgical method for maintaining a space between two vertebral bodies, the method may include the step of obtaining a medical device having a body member with at least one side member engaging the body member. Also included is at least one movement mechanism engaging the at least one side member and the body member. The method may include the step of inserting and coupling an expansion tool into an opening within the medical device and also slidingly inserting the medical device into a space between two vertebral bodies. The method may include the further step of rotating the expansion tool to move the at least one side member in a direction either away from or towards the body member.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

DETAILED DESCRIPTION FOR CARRYING OUT THE INVENTION

Generally stated, disclosed herein is an interbody fusion device or interbody device that typically includes a body member, a threaded rod member, a circular gear face, a support means, and a retractable member. The retractable member extending in a horizontal direction. As used herein, the terms "interbody fusion device," "medical device," "device," "interbody device" and "implant" may be used interchangeable as they essentially describe the same type of device. Further, a corresponding expansion tool used for expansion and contraction of the interbody device is discussed. Finally, described herein is a surgical method for using the interbody fusion device to maintain a space between two vertebral bodies within a patient suffering from a diseased or damaged disc or spinal column.

Figure 1:
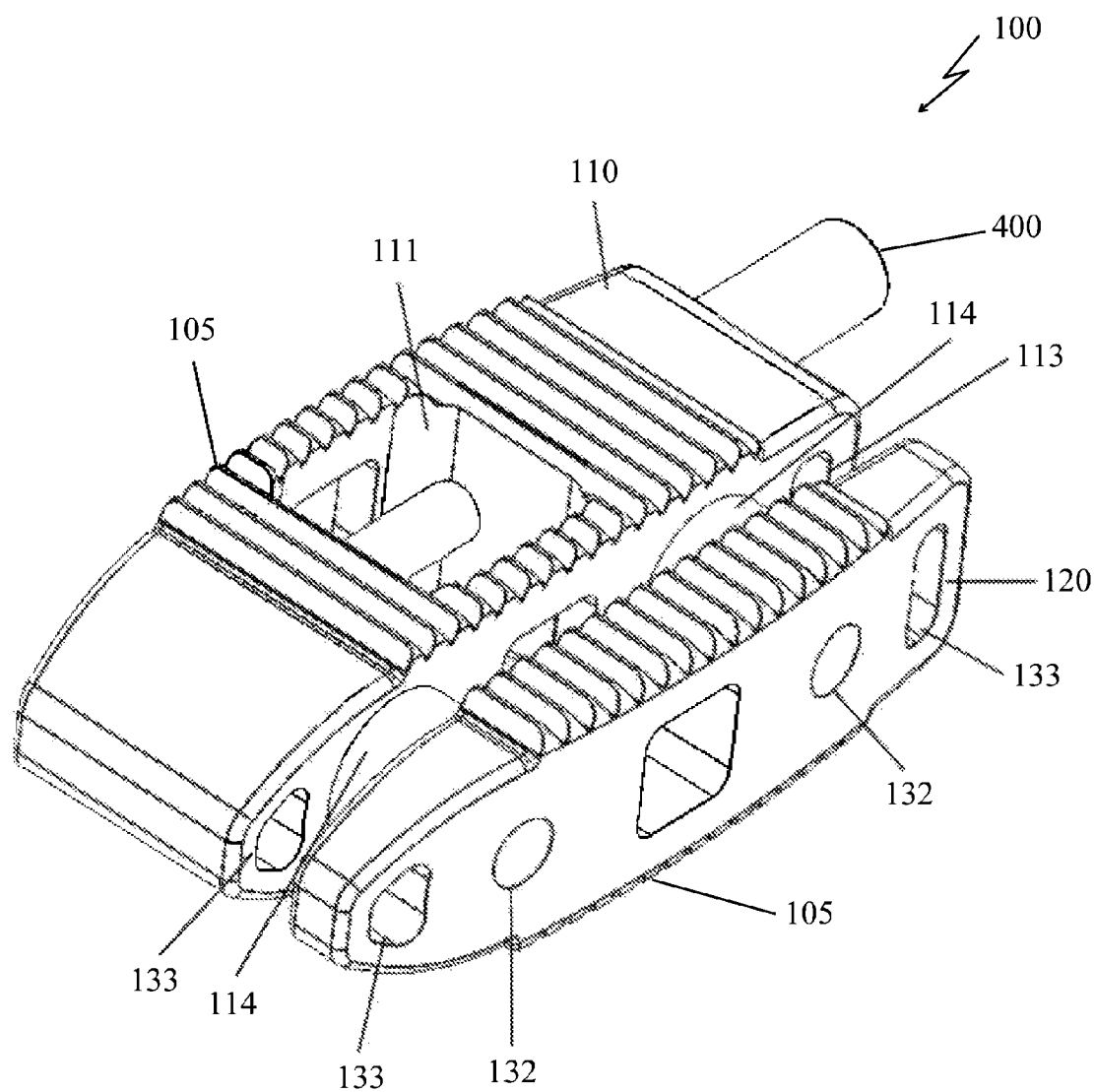
FIG. 1 is a perspective view of one embodiment of a unilateral, horizontal expandable interbody fusion device, in accordance with an aspect of the present invention.

As depicted in FIG. 1, the general arrangement of a unilateral horizontal expandable interbody fusion device 100, in accordance with an aspect of the present invention, includes a body member 110 and one side member 120. In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 2:
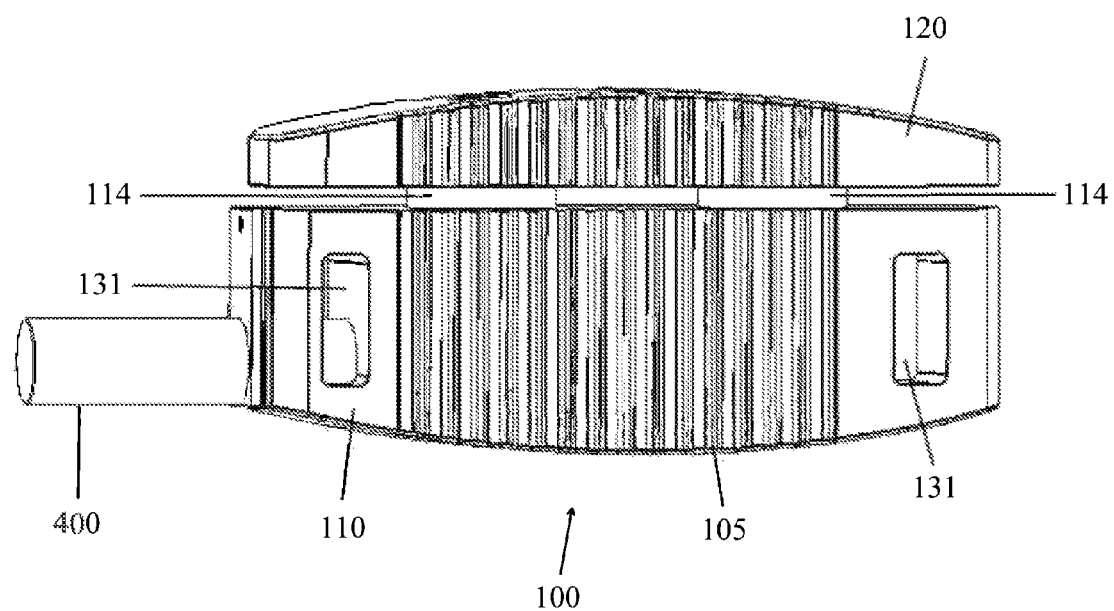
FIG. 2 is an inferior view of another embodiment unilateral, horizontal expandable interbody fusion device with the moveable member retracted, in accordance with an aspect of the present invention.

It is shown in FIG. 1, the example of the unilateral, horizontal expandable interbody fusion device 100. The device 100 as seen in FIGS. 1 and 2 may have, for example, a generally rectangular geometry with various configured long sides to facilitate insertion and bone coverage. Although it would be understood by one skilled in the art that other outside configurations can be used. For example purposes, the long sides are arcuate although it is contemplated that other geometrical shapes may also be used in the construct. The implant 100 may likely include at least one moveable side member 120 and a body member 110. The side member 120 may be detachably coupled to the body member 110.

Figure 3:
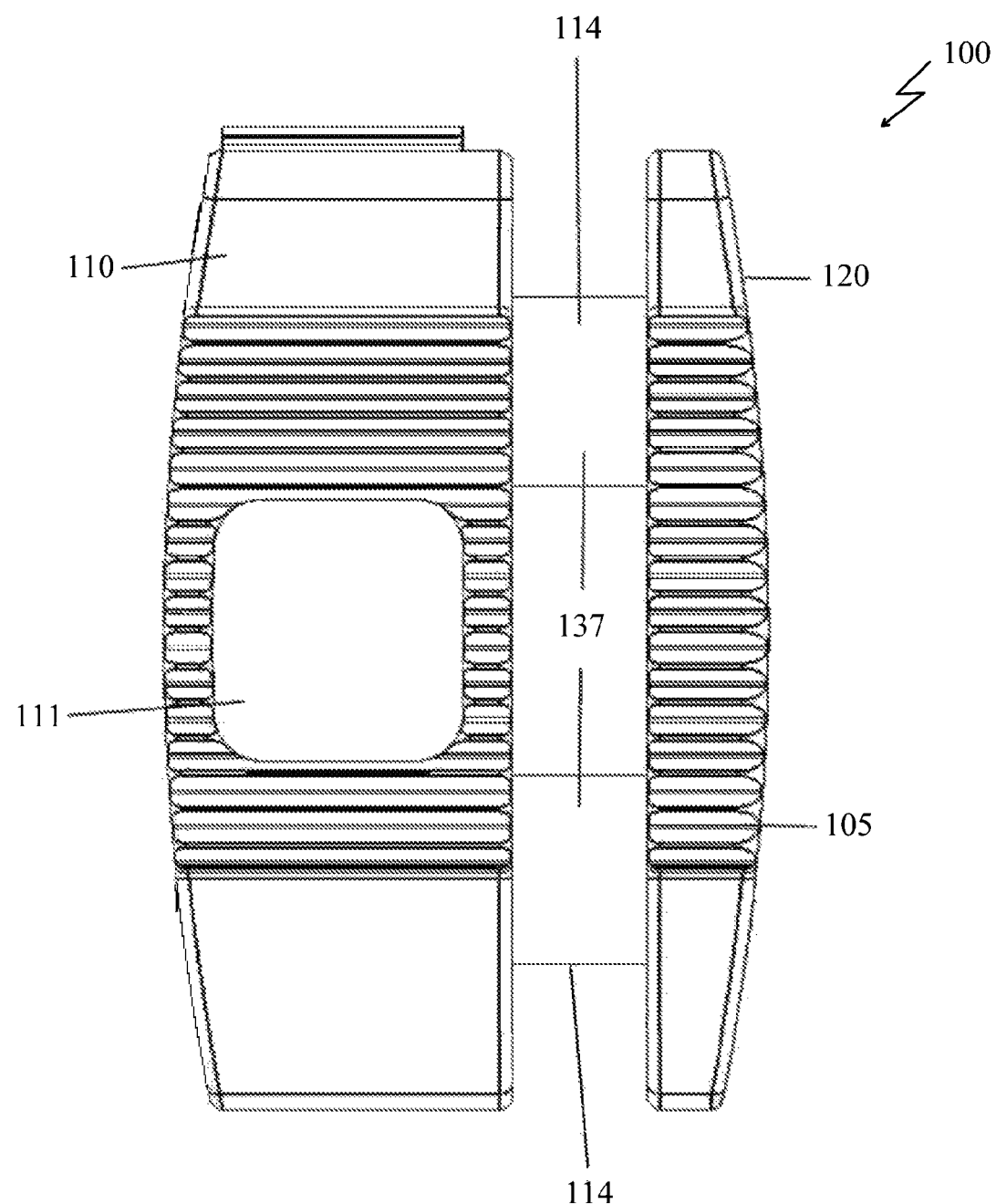
FIG. 3 is a superior view of the expandable interbody fusion device of FIG. 1 with the moveable member extended, in accordance with an aspect of the present invention.
Figure 7:
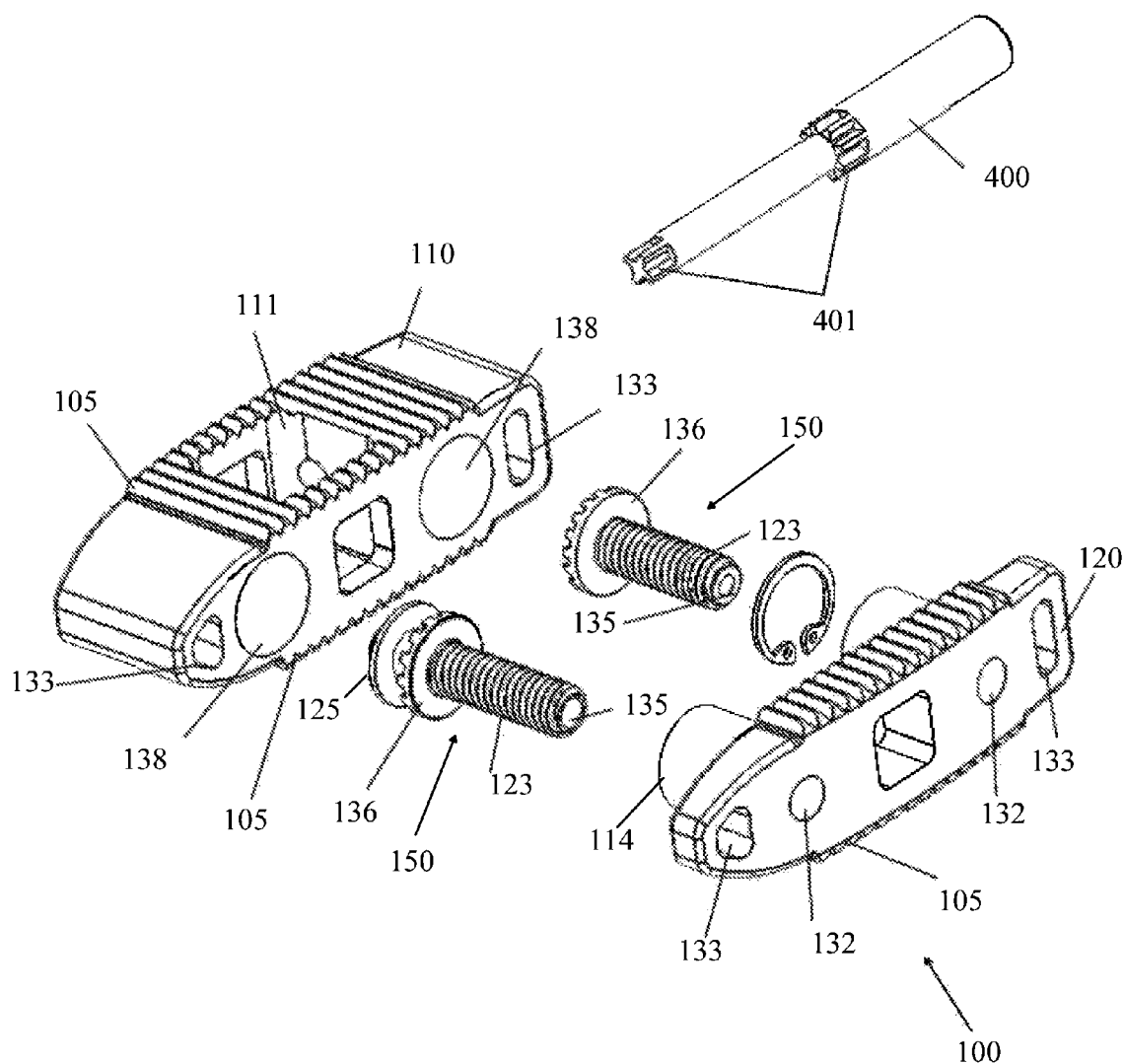
FIG. 7 is a side, exploded view of the expandable interbody fusion device of FIG. 1 and the expansion tool, in accordance with an aspect of the present invention.

As seen in FIGS. 1, 3 and 7, body member 110 may have at least one through hole 111 for insertion of bone graft material disposed on the inferior and superior bone contacting surfaces 105. The hole 111 may extend through the top and bottom surfaces 105 of the body member 110. The opening 111 typically extends through both bone contacting surfaces 105 and into the inner cavity of the body member 110. The size and configuration of the opening 111 allow the surgeon to place bone graft material inside the implant 100 to achieve a continuous fusion between the inferior and superior vertebral bodies.

As shown in FIG. 2, an alternative embodiment of body member 110 may also have at least two marginalized openings 131 that may generally extend through the top and bottom surfaces 105 of the body member 110 and through the inner cavity of the body member 110. The size and configuration of the openings 131 allow the surgeon to pack bone graft material inside the implant 100 to achieve a continuous fusion between the inferior and superior vertebral bodies.

Figure 4:
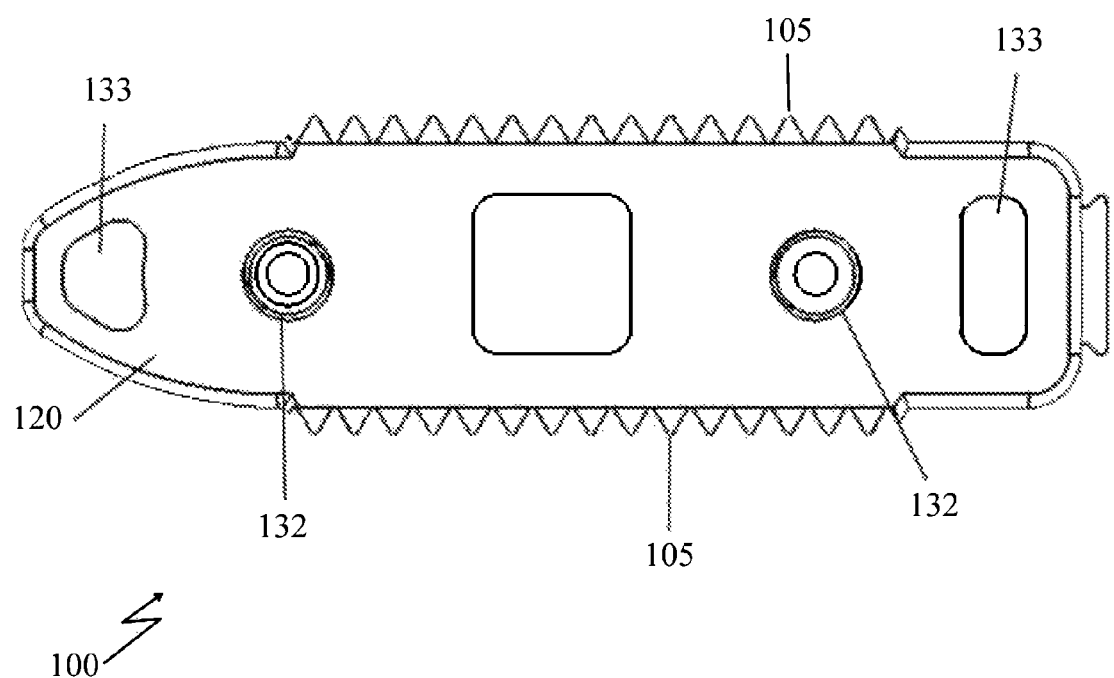
FIG. 4 is a side view of the expandable interbody fusion device of FIG. 1, in accordance with an aspect of the present invention.

As seen in FIGS. 1, 4 and 7, side member 120 also may have at least two holes 132 oriented in a horizontal direction. These holes 132 may be encircled by a cylindrical wall 114 projecting from an inner surface of side member 120 to facilitate the orientation of the side member 120 when it translates from a refracted to an expanded position and vice-a-versa. The wall 114 may also include a stop mechanism which may include a horizontal slot and pin arrangement that keeps the side member 120 from overextending and becoming disengaged with the body member 110.

Figure 8:
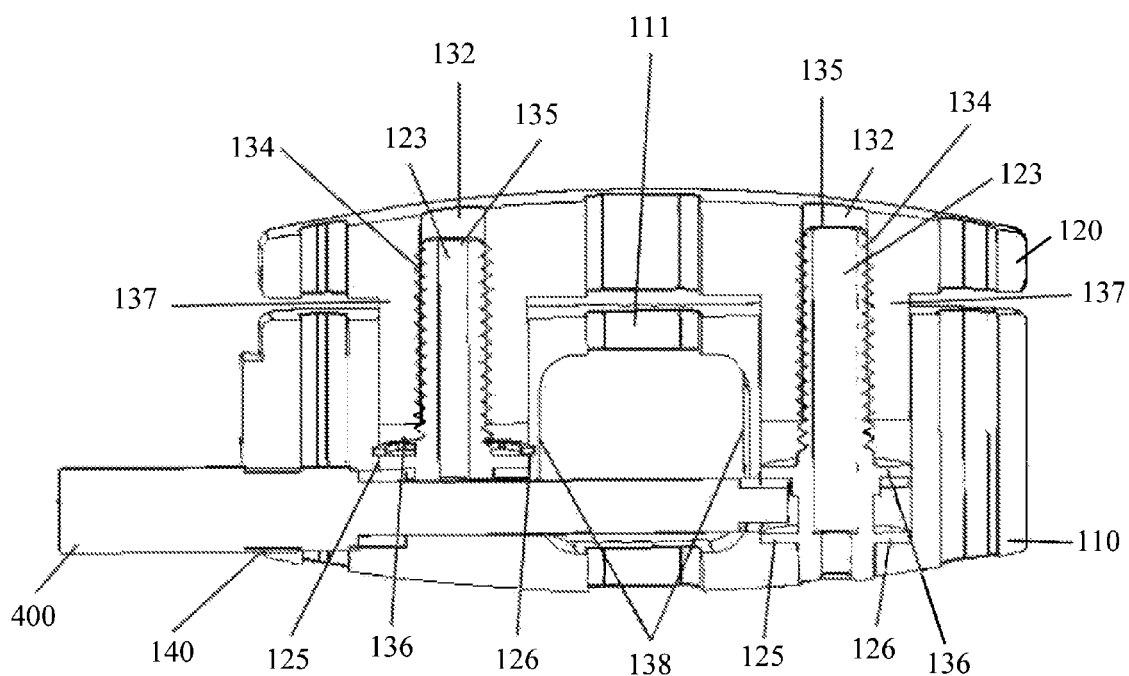
FIG. 8 is a cross-sectional view along the transverse plane of the expandable interbody fusion device of FIG. 1 and the expansion tool, in accordance with an aspect of the present invention.

As shown in the sectional view shown in FIG. 8, holes 132 include a means for moving the side member 150. For example purposes, the means for moving the side member 150 may include sets of threads 134 disposed on the inner surface of holes 132 that are positioned within the side member 120. The threads 134 are configured to threadingly engage with at least two threaded rod members 123. Rotation of threaded rod members 123 will cause side member 120 to move either in an inward or outward direction relative to the body member 110. The overall width of the implant 100 can be changed via the rotation of the threaded rod members 123 and the corresponding unilateral movement of side member 120. It is contemplated that other means for causing the controlled translation of side member 120 to occur may include a ratcheting or a locking sliding mechanism.

Figure 6:
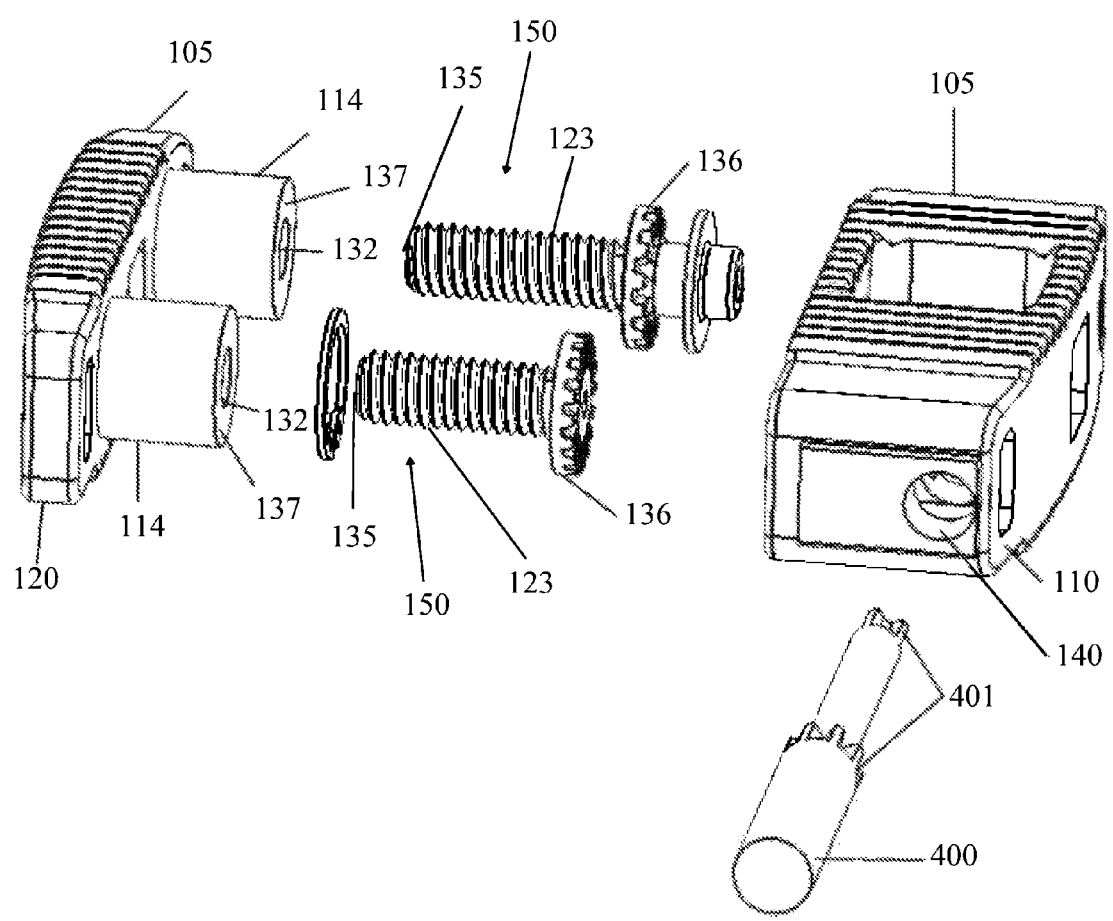
FIG. 6 is a front, exploded view of the expandable interbody fusion device of FIG. 1 and an expansion tool, in accordance with an aspect of the present invention.

As seen in FIGS. 6 and 7, threaded rod members 123 include a cylindrical portion 135 and a gear face or gear 136 with teeth. The means for moving the side member 150 acts to convert rotational movement into translational movement. When assembled within body member 110, both gear faces 136 are turned at the same time with a tool 400. Rotation of the gear faces 136 causes the threaded cylindrical portion 135 to turn, resulting in the translational movement of the side member 120 relative to the body member 110.

Also shown in FIGS. 1, 2, 3 and 4 are the superior and inferior bone contacting surfaces 105. For example purposes, bone contacting surfaces 105 are shown having teeth-like or tine structures projecting away from the superior and inferior surfaces. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. Further, it is contemplated that angled bone contacting surfaces, caps or plates may be attachable to address various clinical deformities that are encountered clinically. It is also understood that the bone contacting surfaces 105 may be coated with bioactive or bone ingrowth coatings.

As shown in FIGS. 2 and 3, body member 110 may have, for example, a generally rectangular shape with, for example, an arcuate outer side and a planar inner side that is positioned adjacent to side member 120 when device 100 is in the fully retracted position. Side member 120 may also have, for example, a planar inner side and an arcuate outer side.

Figure 5:
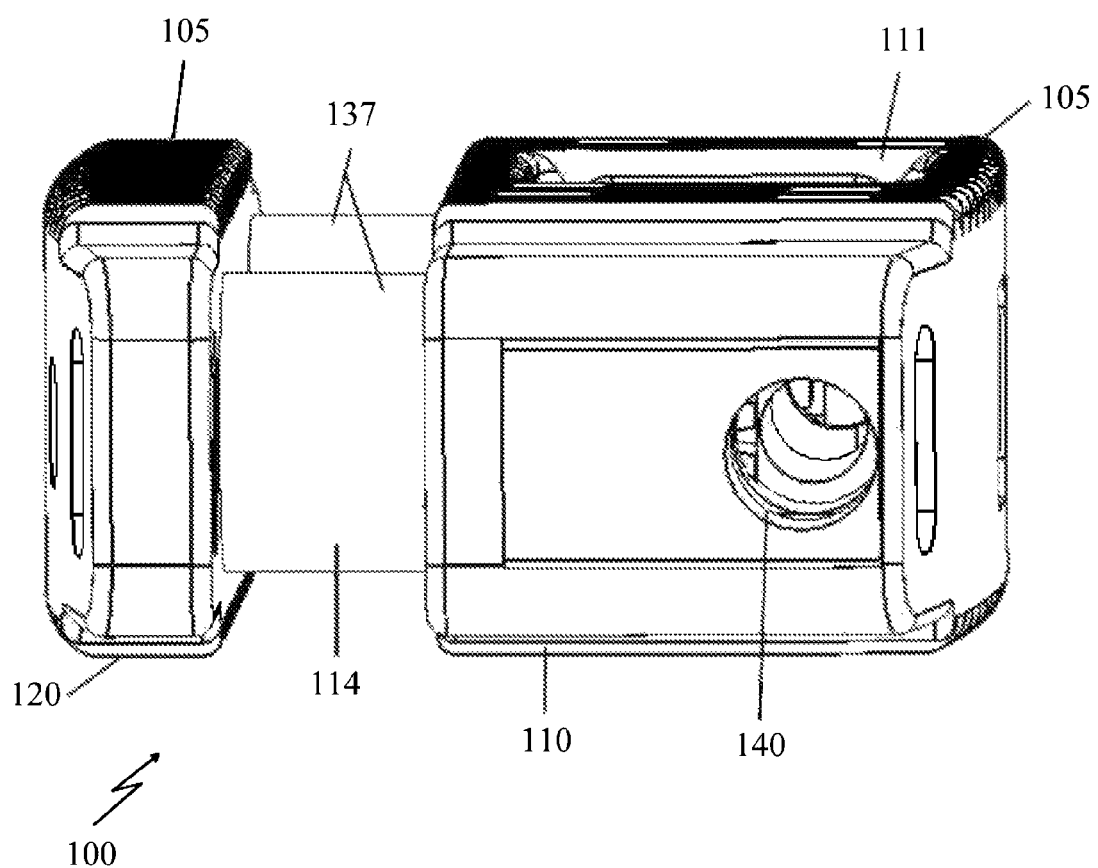
FIG. 5 is a front view of the expandable interbody fusion device of FIG. 1 with the moveable member extended, in accordance with an aspect of the present invention.

FIGS. 3 and 5 show device 100 in its expanded position with housings 137 with outer wall 114 that included inner threaded holes 132 spanning the gap between side member 120 and body member 110. Housings 137 are received into corresponding openings 138 (see FIGS. 7 and 8) in body member 110 when side member 120 is retracted and function to maintain alignment of the side member 120 both in the expanded and retracted positions.

FIG. 4 is a side view of device 100 and shows the ridged bone contacting surfaces 105. Except for the front aspect, the top and bottom surfaces 105 appear to be substantially parallel to each other. It would be understood by one skilled in the art that such surfaces could also, for example, be tapered or angled to address certain anatomic situations. As noted above, the front aspect of device 100 is shown to be tapered to facilitate insertion into the intravertebral space. Several openings 133 are shown that horizontally transverse both the side member 120 and body member 110. Openings 133 are typically filled with bone grafting material following the implantation of the device 100 in vivo. Openings 133 are also illustrated in FIG. 1 as openings 133 and opening 113, where the opening 113 within the body member 110 is the extension of one of openings 133 in the side member 120 through to the body member 110.

The sectional view of FIG. 8, shows the two threaded rod members 123 in position within the body member 110 while engaging the threaded hole 132 of the side member 120 causing movement thereof. FIG. 8 shows housing 137 inside openings 138 with a threaded hole 132 passing down the center of housing 137. A support ring 125 acts to couple the threaded rods 123 to maintain the static position of the means for moving the side member 150 when rotated. Support ring 125 may, for example, be a snap ring or other similar type of structure that will nest within a notch 126 or other retainment mode within the inner cavity of the body member 110.

The device 100 also has a tool opening 140 (see FIGS. 5, 6 and 8) that is sized to receive the expansion tool 400. The tool 400 has two sets of teeth or cogs 401 that correspond to the teeth on the gear face 136. The end of such a tool 400 would usually be inserted into opening 140 and with the two sets of teeth 401 engaging the teeth disposed on the two gear faces 136 of the means for moving the side member 150. Rotation of the tool 400 by the user will cause both gear faces 136 to rotate causing side member 120 to move as the two threaded rod members 123 are actuated. The sectional view seen in FIG. 8 shows the inserted tool 400 with the two gear elements 401 engaged with the two corresponding gear faces 136 of the threaded rods 123.

The biocompatible materials used to fabricate the dynamic horizontal implant 100 could include, for example, a myriad of metals, polymers and composites. Examples of these include PEEK, titanium and stainless steel.

The example surgical method for using the interbody fusion devices 100 is well known in the art, including the appropriate surgical exposure and dissection techniques. The method includes, obtaining the properly sized and configured device 100 relative to the target vertebral end plates that will be opposing the superior and inferior surfaces 105. An expansion or extension tool 400 is then inserted into the hole 140 of the device 100 to secure it for insertion into the spine. For example purposes only, we shall describe herein the technique as used in the insertion between two vertebral bodies to maintain the disc space there between. The device 100 is usually slid from a lateral or posterior-lateral direction into the target disc space.

Following positioning of the device 100 within the disc space, the extension/expansion/insertion tool 400 is rotated causing the side member 120 to move away from the body 110 resulting in the overall width dimension of the device 100 to increase or decrease, depending upon the direction of the rotation of the extension/contraction means 150. The user will stop rotating the extension/expansion tool 400 once optimum support is achieved relative to the inferior and superior vertebral bodies.

The method may further include the step of detaching the extension/expansion tool 400 from the body member 110 and removing the instrument from inside the living body.

It should be understood by those skilled in the art that the surgical method described herein may also include alternatively, using modular bone contacting plates or surfaces which have been coupled in some manner to an alternative embodiment of the body member 110 or side member 120 to accommodate various clinical deformities or bone growth coatings.

Referring now to FIGS. 9-16, another embodiment of a unilateral expandable interbody fusion device 200 is shown. The implant 200 may likely include at least one moveable side member 202 and a body member 204. The side member 202 may be detachably coupled to the body member 204. The body member 204 may include a center through hole 206 and at least two lateral through holes 208 extending through the top and bottom bone contacting surfaces 210. The through holes 206, 208 may allow for insertion of bone graft material to achieve a continuous fusion between the inferior and superior vertebral bodies.

As seen in FIGS. 13-16, the body member 204 may include a medial reinforcement bar 224 on the medial side of the through hole 206 and two lateral bars 226 on the medial side of the through holes 208. The side member 202 also may have a medial channel 228 and at least two side channels 230 oriented in the horizontal direction. The channels 228, 230 are configured to facilitate the orientation and alignment of the side member 202 as it translates from a retracted to an expanded position and vice-a-versa. As the side member 202 is moved relative to the body member 204, the reinforcement bar 224 and two lateral bars 226 engage the center channel 228 and two side channels 230, respectively, in the side member 202. The implant 200 may also include at least one mechanism which may be in the form of a screw, stop pin, flange, lip, clip, or other mechanism that keeps the side member 202 from overextending and disengaging from the base member 204.

Figure 16:
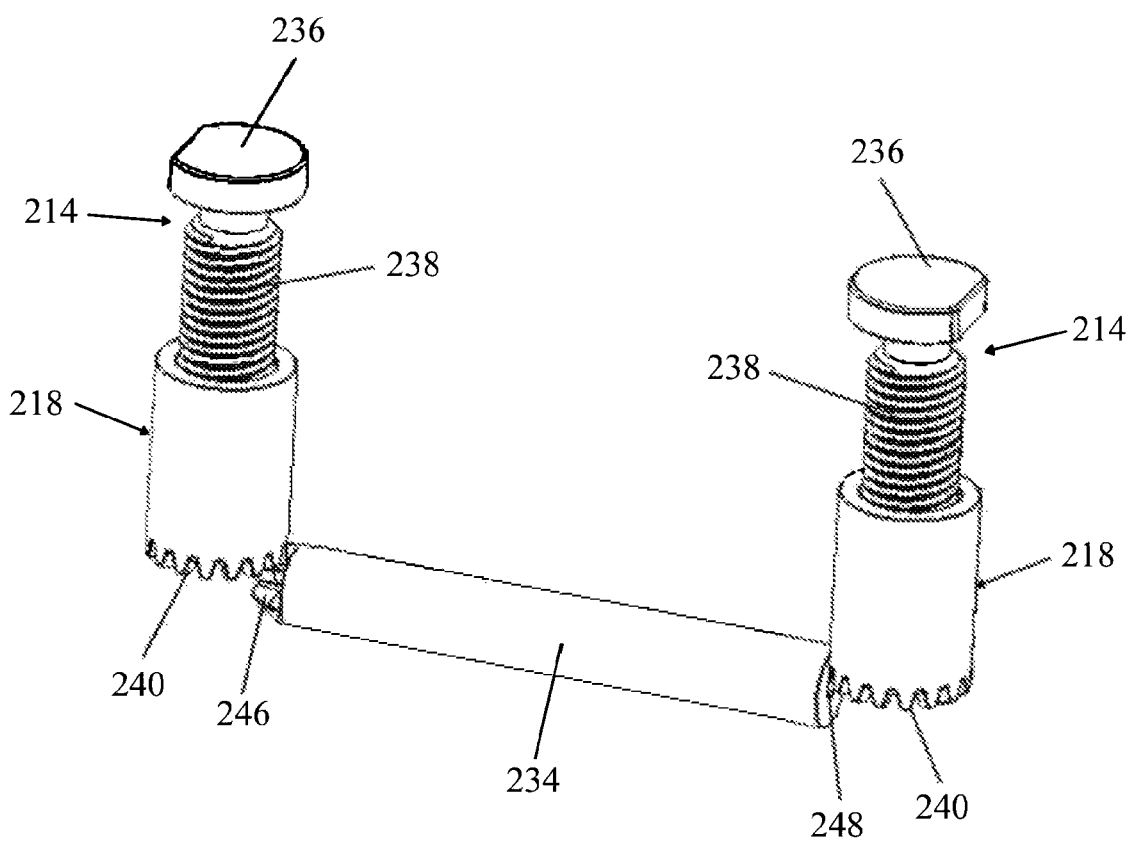
FIG. 16 is a perspective view a movement mechanism of the expandable interbody fusion device of FIG. 9, in accordance with an aspect of the present invention.

Referring now to FIGS. 9 and 13-16, the implant 200 may also include at least one movement mechanism 232. As best seen in FIG. 16, the at least one movement mechanism 232 may, for example purposes, include two screws 214, two threaded sleeves 218, and a gear rod 234 for extension and retraction of the side member 202 relative to the body member 204. The movement mechanism 232 is configured to change rotational movement into translational movement. The movement mechanism 232 may also contain the rotation mechanism 300. The gear rod 234 may include gear teeth 246 on a first end and an opening 248 on a second end. The screws 214 may have a head 236 on a first end and a threaded shaft 238 on a second end. The threaded sleeves 218 may include an interior threaded portion 220 that is configured to engage with the screws 214 and a gear face 240 on the inferior end of the threaded sleeves 218 that is configured to engage the gear teeth 246 on the gear rod 234. The interior threaded portion 220 of the threaded sleeves 218 are configured to mate with the threaded shaft 238 of the screws 214. The interior threaded portion 220 of the threaded sleeves 218 may be completely threaded or only partially threaded. Rotation of the gear rod 234 will cause the threaded sleeves 218 to rotate which will in turn cause the screws 214 to move either in an inward or outward direction relative to the body member 204 thereby extending or retracting the side member 202 with the screws 214. As the side member 202 is extended or retracted the width of the overall implant 200 will change. The side member 202 may also be extended or retracted by other means including, for example, a ratcheting or locking sliding mechanism.

Figure 9:
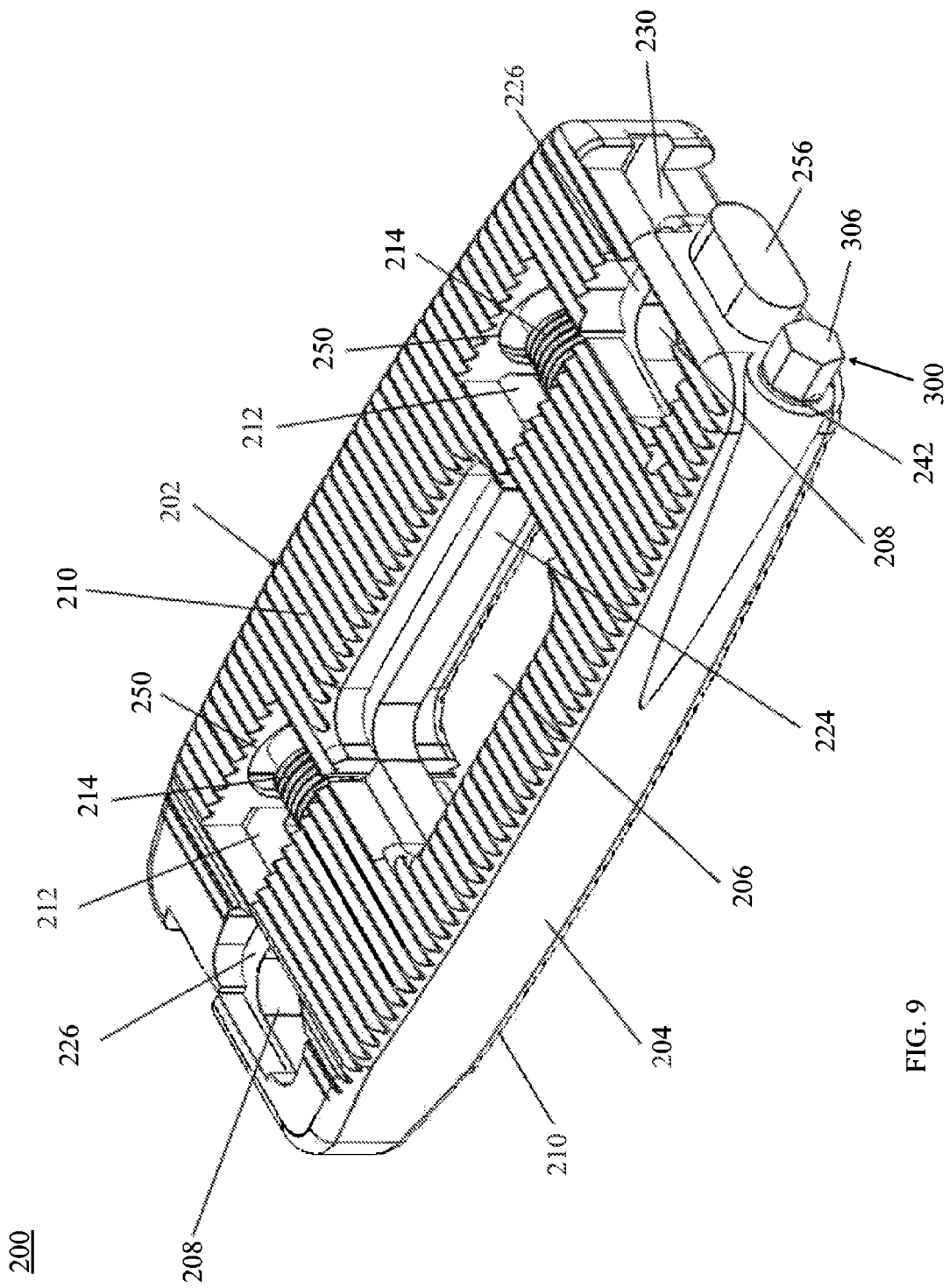
FIG. 9 is a perspective view of another embodiment of a unilateral expandable interbody fusion device, in accordance with an aspect of the present invention.
Figure 10:
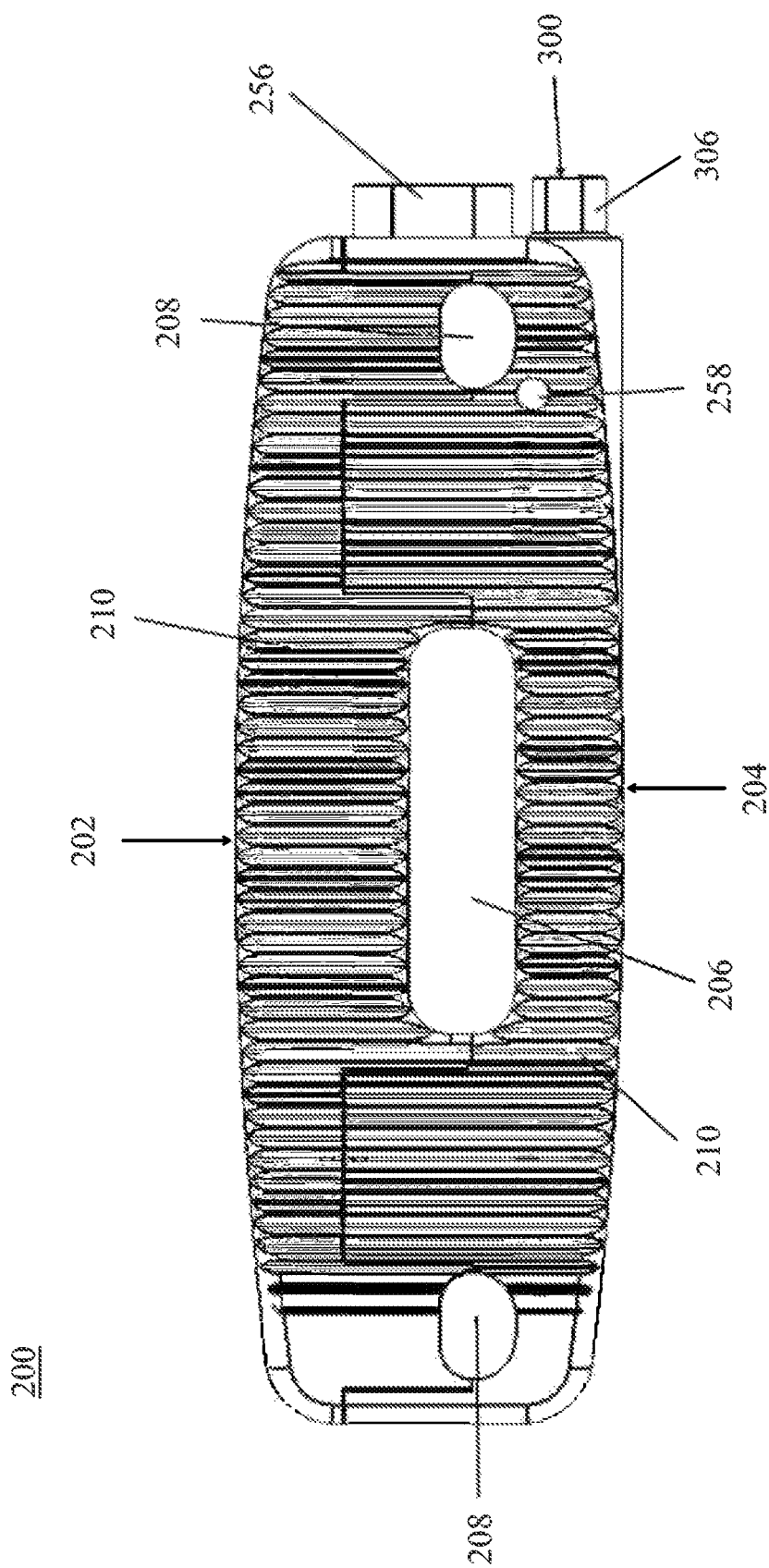
FIG. 10 is a superior view of the expandable interbody fusion device of FIG. 9 with the moveable member completely retracted, in accordance with an aspect of the present invention.
Figure 11:
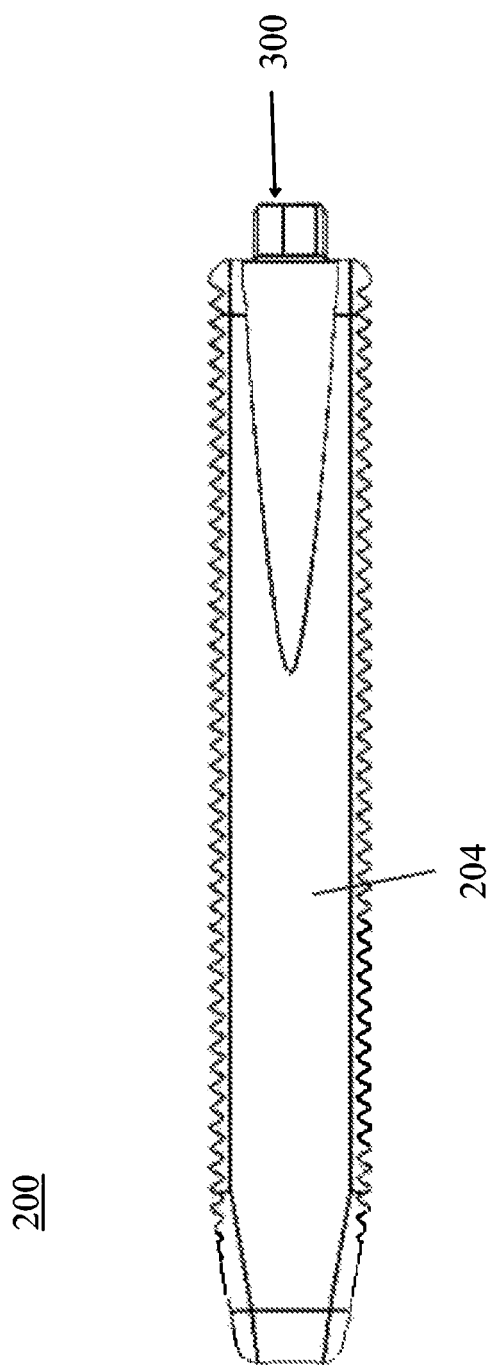
FIG. 11 is a side view of the expandable interbody fusion device of FIG. 9, in accordance with an aspect of the present invention.
Figure 12:
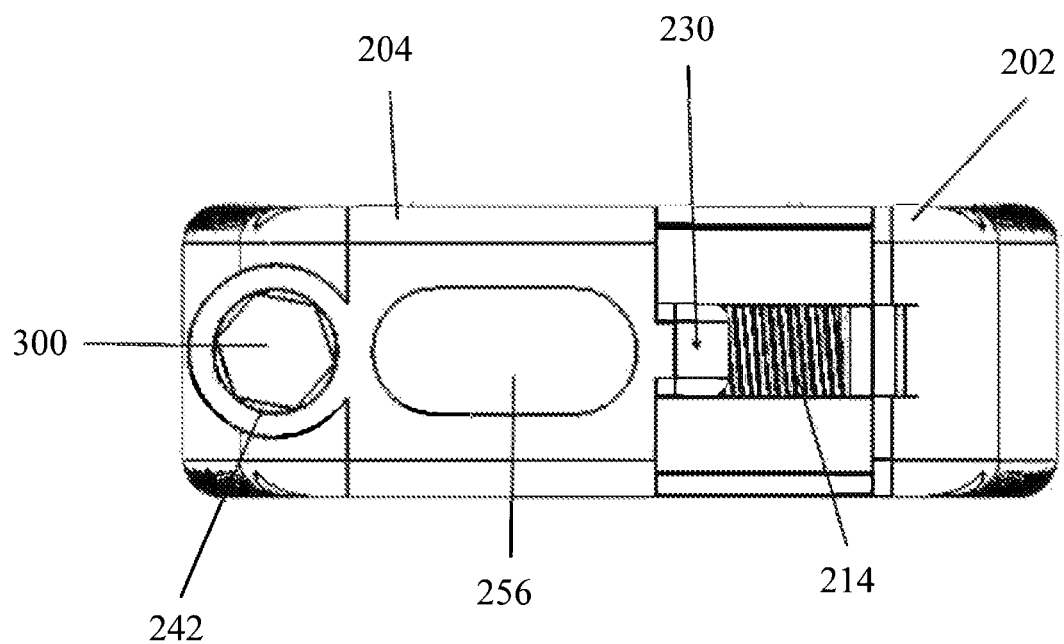
FIG. 12 is a front view of the expandable interbody fusion device of FIG. 9 with the moveable member partially extended and the tool inserted, in accordance with an aspect of the present invention.
Figure 13:
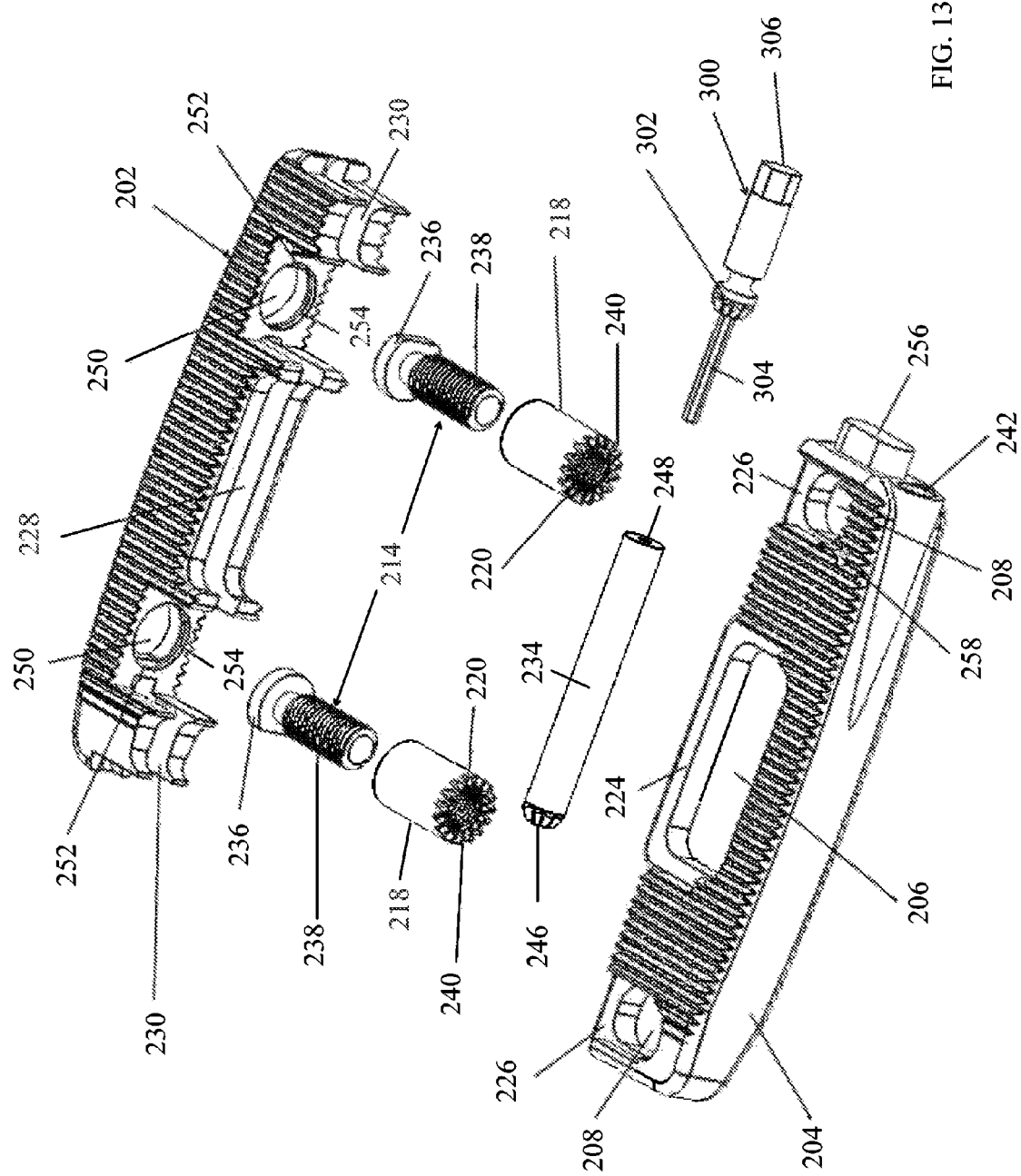
FIG. 13 is a side, exploded view of the expandable interbody fusion device of FIG. 9 and the tool, in accordance with an aspect of the present invention.

The gear rod 234 may be inserted into the opening 242 as shown in FIGS. 9 and 12-13. The opening 242 runs along the longitudinal axis of the body member 204. The body member 204 may also include two horizontal openings 216 that may be positioned adjacent the through hole 206 and one of the through holes 208 in the body member 204. The two openings 216 may extend along the lateral axis of the body member 204 and terminate in the opening 242. The openings 216 are configured to house threaded sleeves 218. The openings may also have a groove or rim 244 near the openings 216 for inserting a fastener, such as a c-clip, snap ring, or the like, to secure the threaded sleeves 218 within the openings 216. The rim 244 and/or fastener inserted into the rim 244 are configured to mate with a corresponding bearing surface on the threaded sleeves 218. The movement mechanism 232 for extension and retraction of the side member 202 relative to the body member 204 may be received within the openings 216 and the openings 212. The two openings 212 are exposed when the side member 202 is extended away from the body member 204.

Figure 14:
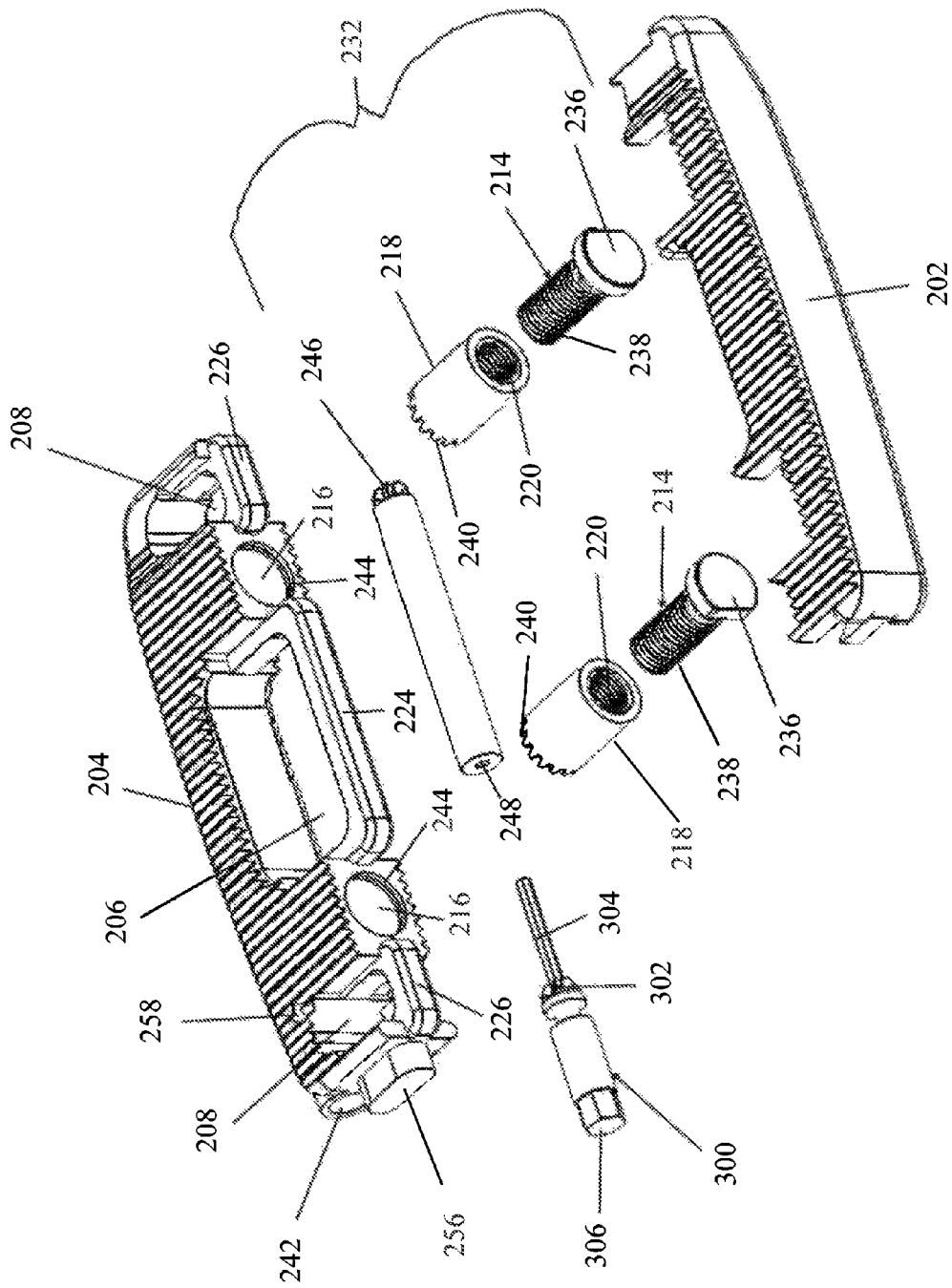
FIG. 14 is another side, exploded view of the expandable interbody fusion device of FIG. 9 and the expansion tool, in accordance with an aspect of the present invention.
Figure 15:
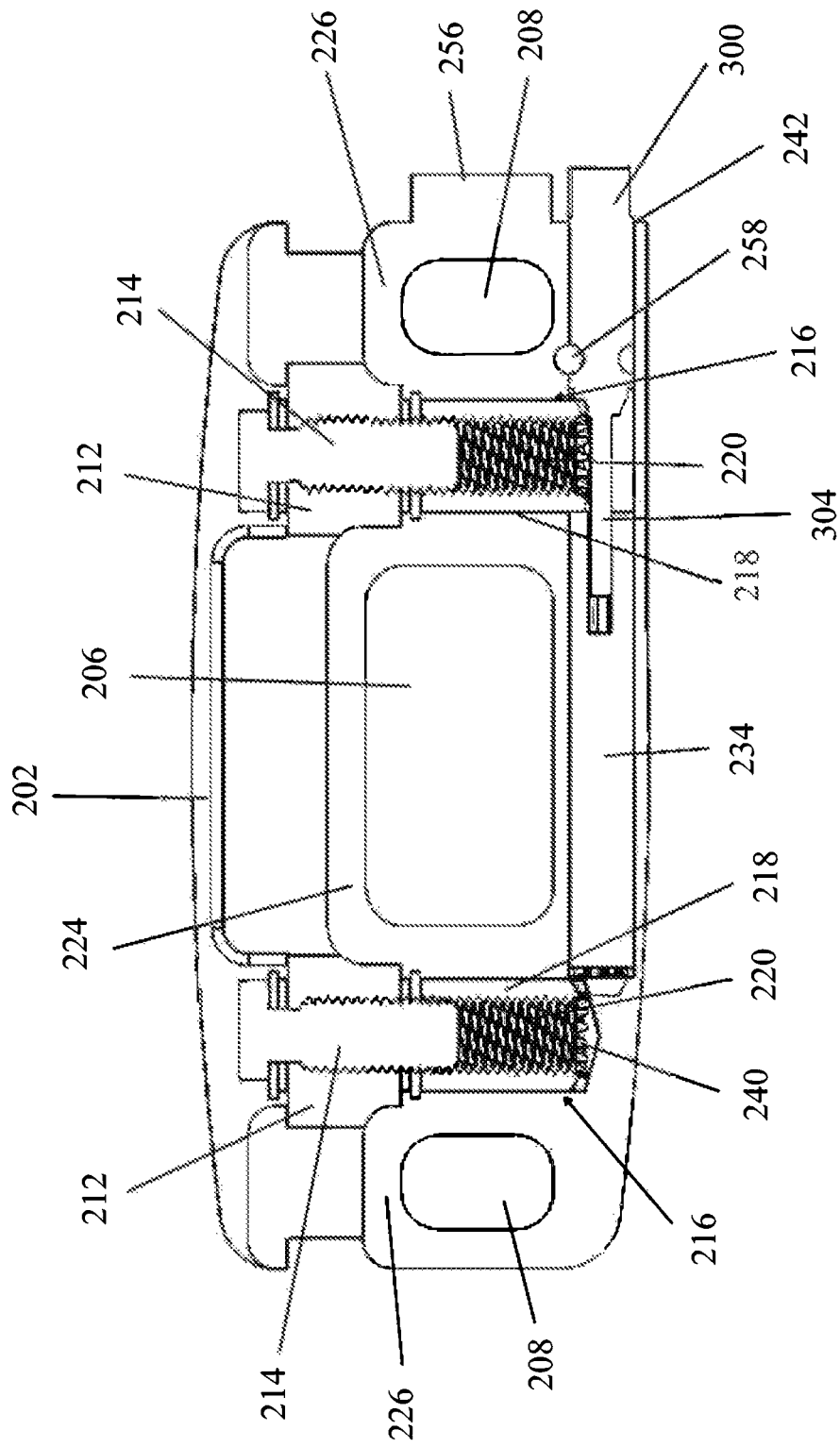
FIG. 15 is a cross-sectional view along the transverse plane of the expandable interbody fusion device of FIG. 9 and the expansion tool, in accordance with an aspect of the present invention.

The head 236 of the screws 214 may be removably secured in the openings 250 on the interior surface of the side member 202, as shown in FIGS. 13 and 14. The screws 214 may be secured in the openings 250 with a fastener, for example, a pin, clip, or the like. The openings 250 may include a groove or rim 254 to retain the fastener and thereby removably secure the screws 214 to the side member 202. The heads 236 may be generally circular with at least one straight edge for mating with a protrusion 252 in the openings 250 to prevent rotation and maintain the position of the screws 214 as the threaded sleeves 218 rotate. The heads 236 may also have other configurations, including but not limited to squares, hexagons, and the like which inhibit rotation of the screws 214. The heads 236 of the screws 214 may also be keyed to fit in a specific orientation within the openings 250.

As shown in FIGS. 9-16, a rotation mechanism 300 may be used to expand and retract the side member 202 from the body member 204. The rotation mechanism 300 extends through an opening 242 in the body member 204 which extends from the exterior of the body member 204 to engage the gear rod 234. The rotation mechanism 300 includes a toothed end 302 for mating with the gear face 240 of the threaded sleeves 218 on the posterior side of the implant 200 and a driveshaft 304 which mates with the opening 248 in the gear rod 234. The gear rod 234 in turn extends through the opening 242 from the opening 216 on the posterior side of the implant 200 to the opening 216 on the anterior side of the implant 200 where the gear rod 234 engages the gear face 240 of the threaded sleeve 218 housed in the anterior opening 216. The teeth or cogs 240 of the threaded sleeves 218 are sized to mate with the corresponding toothed end 302 of the rotation mechanism 300 and the gear teeth 246 of the gear rod 234. Rotation of the rotation mechanism 300 by a user may be accomplished by rotating the rotation mechanism 300 at the head 306 which in turn will cause rotation of the toothed end 302 of the rotation mechanism 300 causing the posterior threaded sleeve 218 and the gear rod 234 to rotate thereby rotating the anterior threaded sleeve 218. Rotation of the threaded sleeves 218 causes the screws 214 to translate in the threaded sleeves 218 thereby moving the side member 202. The threaded sleeves 218, screws 214, and gear rod 234 function to convert rotational movement of the rotation mechanism 300 to translational movement of the side member 202 relative to the body member 204. The body member 204 may also include an opening 258 extending through the top and bottom bone contacting surfaces of the body member 204. A fastener, such as a pin, may be inserted into the opening 258 to secure the rotation mechanism 300 to prevent rotation after the desired position is reached. If the rotation mechanism 300 is secured by the fastener to prevent rotation, the rotation mechanism 300 may be left inside of the implant 200 when the patient is closed after the surgery is completed.

An inserter tool may be used to insert the implant 200 into a patient between two adjacent vertebrae. The inserter tool may be removably attached to the implant 200 at an alignment buttress 256 on the posterior portion of the body member 204. The inserter tool may also provide a mechanism to rotate the rotation mechanism 300 after the implant 200 is inserted into the patient. Alternatively, a rotation tool may be used to rotate the rotation mechanism 300 while the inserter tool holds the implant in a desired position.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A surgical method for maintaining a space between two vertebral bodies in a spine, comprising:
    obtaining a medical device comprising:
        a body member;
        at least one side member engaging the body member; and
        at least one movement mechanism engaging the at least one side member and the body member, the at least one movement mechanism including first and second threaded rod members;
    inserting and coupling a tool into an opening within the medical device, the tool including first and second sets of gear teeth;
    slidingly inserting the medical device into a space between two vertebral bodies; and
    rotating the tool to move the at least one side member in a horizontal direction relative to the body member, the rotating the tool including rotating the first threaded rod member with the first set of gear teeth and rotating the second threaded rod member with second set of gear teeth.

2. The method of claim 1, wherein the method further comprises inserting bone graft material into the medical device.

3. The method of claim 1, wherein the method further comprises detaching the tool from the medical device and removing the tool from the space between the two vertebral bodies in the spine.

4. The method of claim 1, wherein the at least one movement mechanism includes first and second threaded sleeves, and wherein rotating the tool includes rotating the first threaded sleeve of in coordination with the second threaded sleeve.

5. The method of claim 4, wherein the at least one movement mechanism further includes a gear rod drivingly engaged with the second threaded sleeve, and wherein rotating the tool includes:
rotating the first threaded sleeve with the tool; and
rotating the second threaded sleeve with the gear rod.

6. The method of claim 1, wherein the at least one movement mechanism includes first and second screw members and first and second threaded sleeves, and wherein rotating the tool includes threading at least one of the first and second screw members relative to at least one of the first and second threaded sleeves.

7. The method of claim 1, wherein the inserting and coupling the tool includes engaging the first set of gear teeth with a first gear face coupled to the first threaded rod member and engaging the second set of gear teeth with a second gear face coupled to the second threaded rod member.

8. The method of claim 7, wherein the second gear face is offset, in the horizontal direction, from the first gear face.

9. A surgical method for implanting a medical device within a space between two vertebral bodies in a spine, comprising:
obtaining the medical device comprising:
a body member;
at least one moveable member engaging the body member; and
at least one movement mechanism engaging the at least one moveable member and the body member, the at least one movement mechanism including first and second threaded members;
inserting and coupling a tool into an opening within the medical device, the tool including at least a first set of gear teeth;
slidingly inserting the medical device into a space between two vertebral bodies; and
rotating the tool to move the at least one moveable member in a first direction relative to the body member, the rotating the tool including rotating the first threaded member with the first set of gear teeth and rotating the second threaded member with a second set of gear teeth.

10. The method of claim 9, wherein the inserting and coupling the tool includes engaging the first set of gear teeth with a first gear face on the first threaded member and engaging the second set of gear teeth included on the tool with the a second gear face on the second threaded member.

11. The method of claim 9, wherein the inserting and coupling the tool includes engaging the first set of gear teeth with a first gear face on the first threaded member and engaging a gear rod disposed within the movement mechanism.

12. The method of claim 11, wherein engaging the gear rod includes coupling a drive shaft portion on a distal end of the tool with an opening in a proximal end of the gear rod.

13. The method of claim 11, wherein the gear rod includes the second set of gear teeth engaged with a second gear face on the second threaded member.

14. The method of claim 9, wherein the first threaded member includes a first threaded rod and the second threaded member includes a second threaded rod; and
wherein the inserting and coupling the tool includes:
engaging the first set of gear teeth with a first gear face disposed on a head of the first threaded rod, and
engaging the second set of gear teeth with a second gear face disposed on a head of the second threaded rod.

15. The method of claim 9, wherein the first threaded member includes a first threaded sleeve and the second threaded member includes a second threaded sleeve; and
wherein the inserting and coupling the tool includes:
engaging the first set of gear teeth with a first gear face disposed on a first end of the first threaded sleeve, and
engaging the second set of gear teeth with a second gear face disposed on a first end of the second threaded sleeve.

16. The method of claim 15, wherein engaging the second set of gear teeth includes coupling a drive shaft portion on a distal end of the tool with an opening in a proximal end of a gear rod, wherein the gear rod includes the second gear face disposed on a distal end.

17. The method of claim 9, wherein rotating the tool to move the at least one moveable member in the first direction includes engaging an externally threaded surface of the first threaded member with an internally threaded surface of a first threaded sleeve, and engaging an externally threaded surface of the second threaded member with an internally threaded surface of a second threaded sleeve.

18. The method of claim 9, wherein rotating the tool to move the at least one moveable member in a first direction includes engaging an internally threaded surface of the first threaded member with an externally threaded surface of a first threaded rod within the first threaded member, and engaging an internally threaded surface of the second threaded member with an externally threaded surface of a second threaded rod within the second threaded member.

* * * * *